US012660990B2

(12) United States Patent
Chu et al.

(10) Patent No.: US 12,660,990 B2
(45) Date of Patent: Jun. 23, 2026

(54) LENS MODULE

(71) Applicant: HUKUI BIOTECHNOLOGY CO., LTD., Taipei City (TW)

(72) Inventors: Yi-Ming Chu, Taipei City (TW); Ming-Kun Chan, Taipei City (TW)

(73) Assignee: HUKUI BIOTECHNOLOGY CO., LTD., Taipei City (TW)

( * ) Notice: Subject to any disclaimer, the term of this patent is extended or adjusted under 35 U.S.C. 154(b) by 134 days.

(21) Appl. No.: 18/736,568

(22) Filed: Jun. 7, 2024

(65) Prior Publication Data

US 2024/0415374 A1 Dec. 19, 2024

Related U.S. Application Data

(60) Provisional application No. 63/508,510, filed on Jun. 16, 2023.

(30) Foreign Application Priority Data

Apr. 15, 2024 (TW) ................................. 113113945

(51) Int. Cl.
*A61B 1/00* (2006.01)
(52) U.S. Cl.
CPC ...... *A61B 1/00193* (2013.01); *A61B 1/00183* (2013.01)
(58) Field of Classification Search
CPC ............ A61B 1/00183; A61B 1/00188; A61B 1/00193; A61B 1/00194; H04N 13/128; H04N 13/239
See application file for complete search history.

(56) References Cited

U.S. PATENT DOCUMENTS

| | | | | |
|---|---|---|---|---|
| 4,846,155 A | * | 7/1989 | Kimura .............. | A61B 1/00188 |
| | | | | 348/E5.045 |
| 5,743,846 A | * | 4/1998 | Takahashi .......... | G02B 23/2415 |
| | | | | 600/166 |
| 2008/0045789 A1 | * | 2/2008 | Sawachi .................. | G02B 7/28 |
| | | | | 600/137 |
| 2014/0210945 A1 | * | 7/2014 | Morizumi .......... | A61B 1/00188 |
| | | | | 348/45 |

(Continued)

FOREIGN PATENT DOCUMENTS

FR 2979054 A1 * 2/2013 ........... A61B 1/0676

*Primary Examiner* — Michael J Carey
*Assistant Examiner* — Stephen Floyd London

(57) ABSTRACT

A lens module conducive to enhancing the quality of images captured by the lens module comprises a substrate, two holders, two image sensors, and two lenses. The lens module includes a substrate; two holders disposed on the substrate; two image sensors disposed on the substrate and disposed in the two holders respectively; and two lenses disposed in the two holders respectively. The optical axes of the two lenses pass through the two image sensors respectively and meet in front of the substrate. An angle retaining seat having two adjoining surfaces, the two adjoining surfaces tilting to allow outward opposing edges of the two adjoining surfaces to be higher than inward opposing edges of the two adjoining surfaces. The angle retaining seat has two piezoelectric layers connected to the two adjoining surfaces and corresponding in position to outward opposing edges.

7 Claims, 5 Drawing Sheets

(56)         References Cited

U.S. PATENT DOCUMENTS

| 2014/0228644 A1* | 8/2014 | Ikenaga | ............. | A61B 1/00193 |
| | | | | 600/166 |
| 2014/0272764 A1* | 9/2014 | Miller | ................... | A61B 1/051 |
| | | | | 433/29 |
| 2015/0156461 A1* | 6/2015 | Jessop | ................. | H04N 13/296 |
| | | | | 348/47 |
| 2018/0270453 A1* | 9/2018 | Kupferschmid | ... | G02B 23/2484 |
| 2020/0178766 A1* | 6/2020 | Ichihara | .............. | A61B 1/0008 |
| 2020/0209730 A1* | 7/2020 | Jones | ................ | A61B 1/00188 |
| 2021/0177555 A1* | 6/2021 | Chang | ................ | A61B 1/00194 |
| 2023/0029750 A1* | 2/2023 | Yamamoto | ......... | G02B 23/2453 |
| 2024/0000296 A1* | 1/2024 | Shafer | ............... | A61B 1/00193 |

* cited by examiner

LENS MODULE

This non-provisional application claims priority under 35 U.S.C. § 119(e) on U.S. provisional Patent Application No. 63/508,510 filed on Jun. 16, 2023, the entire contents of which are hereby incorporated by reference. This non-provisional application claims priority under 35 U.S.C. § 119 (a) on Patent Application No(s). 113113945 filed in Taiwan, R.O.C. on Apr. 15, 2024, the entire contents of which are hereby incorporated by reference.

BACKGROUND OF THE INVENTION

Background of the Invention

1. Field of the Invention

The present disclosure relates to optical modules, and in particular to a lens module with two lenses for capturing images simultaneously.

2. Description of the Related Art

Endoscopes are tubular medical instruments that enter a human body to inspect the interior thereof. In recent years, endoscopes are not only widely used in medical checkup but also in surgery.

Endoscopes are used in minimally invasive surgery that involves much smaller incisions than conventional surgery, less pain, and ease of wound healing, leaving almost no scar. Endoscopic surgery is so popular with medical professionals and patients that various functionally enhanced endoscopes have become key products of research and development performed by medical device manufacturers. Furthermore, the demand for the industrial application of endoscopes is ever-increasing.

Moreover, conventional endoscopes each typically come with one single lens that, in the best possible scenario, has an adjustable focal length for optimizing the sharpness of images captured and enhancing the precision of reading the images. In medical or industrial situations that require high precision of operation, such as minimally invasive brain surgery, images captured by conventional endoscopes lack a three-dimensional sense and thus may result in misjudgment of a surgical site. Therefore, there is still room for improvement of conventional endoscopes.

BRIEF SUMMARY OF THE INVENTION

In view of the aforesaid drawbacks of the prior art, it is an objective of the present disclosure to provide a lens module applicable to endoscopes to capture images having a three-dimensional sense.

Direction-related terms or the like used herein, such as "front", "rear", "left", "right", "upper" (top), "lower" (bottom), "inner", "outer", and "lateral side" are intended to refer to the directions depicted in accompanying drawings. The direction-related terms or the like are aimed at assisting with describing and understanding the embodiments of the present disclosure rather than limiting the present disclosure.

Quantitative terms, such as "one", "a", and "an", are used herein to describe components and elements of the present disclosure merely for the sake of convenience and provides the ordinary meaning of the scope of the present disclosure. In the present disclosure, the quantitative terms must be interpreted to include one or at least one, and every singular noun must be interpreted to include its corresponding plural noun unless stated otherwise.

The meaning of similar expressions used herein, such as "be coupled to", "be fitted to" and "be mounted on", includes options, namely "after being connected, elements can still be separated without being damaged" and "after being connected, elements become inseparable". Persons skilled in the art can select one of the options according to the materials of which the elements to be connected are made or assembly requirements.

To achieve the above and other objectives, the present disclosure provides a lens module, comprising: a substrate; two holders disposed on the substrate; two image sensors disposed on the substrate and disposed in the two holders respectively; and two lenses disposed in the two holders respectively, wherein optical axes of the two lenses pass through the two image sensors respectively and meet in front of the substrate.

In the lens module, the substrate has a first region and a second region, with the first and second regions separated by a partition line of the substrate, the two image sensors are disposed within the first region and the second region respectively. The first region and the second region tilt such that outward opposing edges of the first region and the second region are higher than inward opposing edges of the first region and the second region.

In the lens module, the first region and the second region tilt symmetrically about the partition line.

The lens module further comprises two reinforcing plates connected to a rear surface of the substrate and corresponding in position to the first region and the second region of the substrate respectively.

The lens module further comprises an angle retaining seat having two adjoining surfaces, the two adjoining surfaces tilting to allow outward opposing edges of the two adjoining surfaces to be higher than inward opposing edges of the two adjoining surfaces, allowing a rear surface of the substrate to be directly or indirectly coupled to the two adjoining surfaces.

In the lens module, the angle retaining seat has two piezoelectric layers connected to the two adjoining surfaces and corresponding in position to outward opposing edges thereof respectively.

In the lens module, the angle retaining seat has a direction mark for recognizing a mounting direction of the angle retaining seat.

In the lens module, the holders are made of an opaque material.

In the lens module, the holders each have a central hole and a plurality of adhesive grooves, with the central hole penetrating an outer end surface of the holder, with the plurality of adhesive grooves being disposed on the outer end surface and being in communication with the central hole, allowing the lenses to be penetratingly disposed at the central holes respectively.

The lens module further comprises at least one light source disposed on at least one of the two holders.

Owing to the binocular disparity achieved by the lens module, images captured by the left unit and the right unit have a three-dimensional sense when displayed on an appropriate display device. Therefore, the lens module of the present disclosure is applied to endoscopes for capturing images such that the images thus captured have a stronger three-dimensional sense than images captured by conventional endoscopes, allowing the images thus captured to appear real. The lens module of the present disclosure not only improves the approximation to reality in terms of human perception of the images thus captured but also enhances the precision of various operations and judgements. Thus, endoscopes equipped with the lens module of the present disclosure meet medical or industrial demand associated with strict operational precision requirement, for example, by being applied to minimally invasive brain surgery, for example, for use in brain thrombus removal, and enhancing surgery efficiency and success rate.

DETAILED DESCRIPTION OF THE INVENTION

To facilitate understanding of the object, characteristics, and effects of this present disclosure, embodiments together with the attached drawings for the detailed description of the present disclosure are provided.

Figure 1:
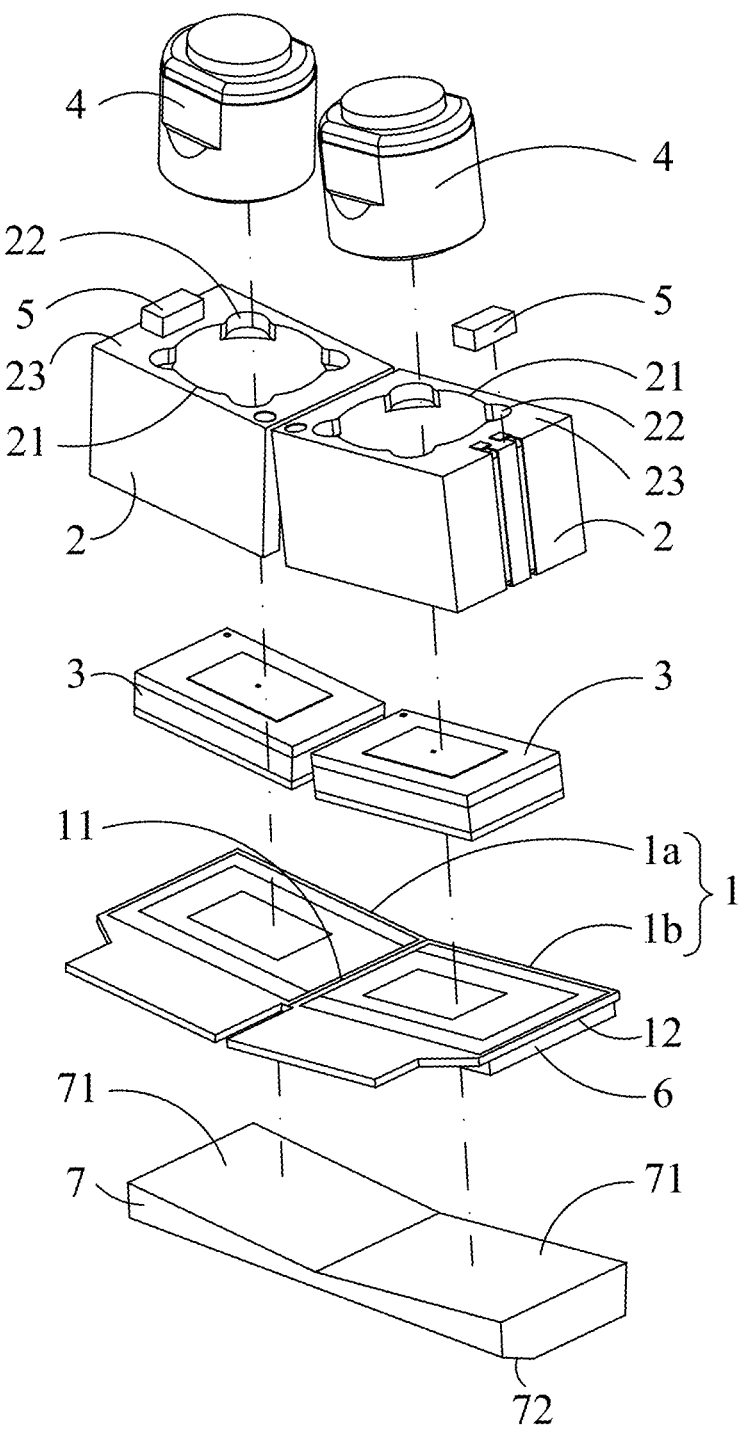
FIG. 1 is an exploded view of a lens module according to an embodiment of the present disclosure.
Figure 2:
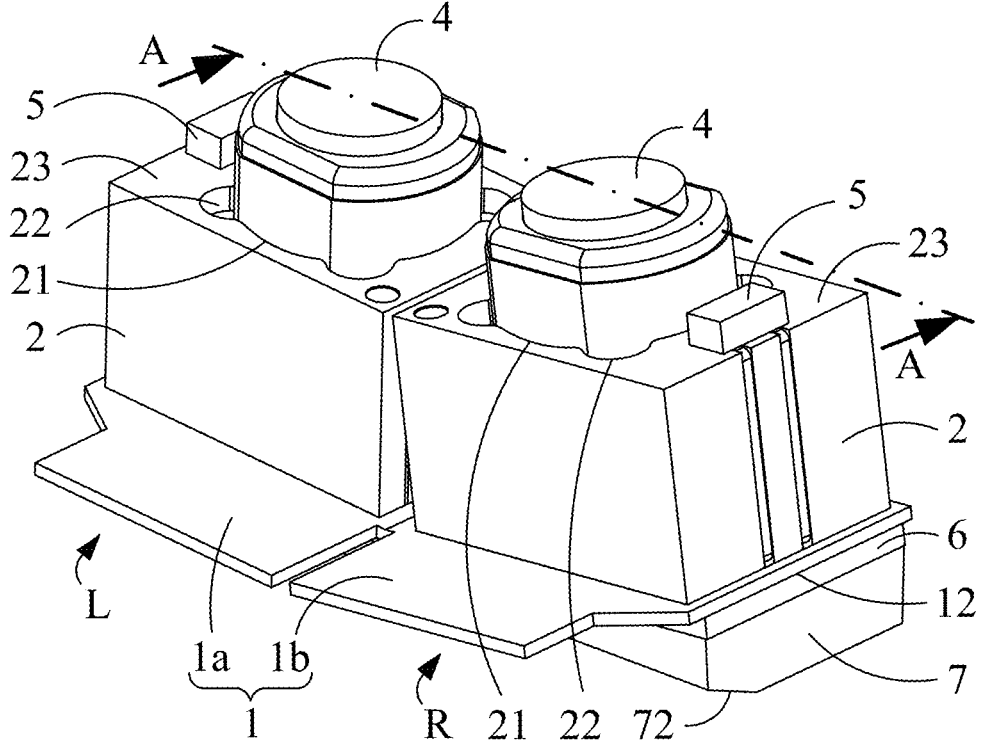
FIG. 2 is a perspective view of the lens module according to an embodiment of the present disclosure.
Figure 3:
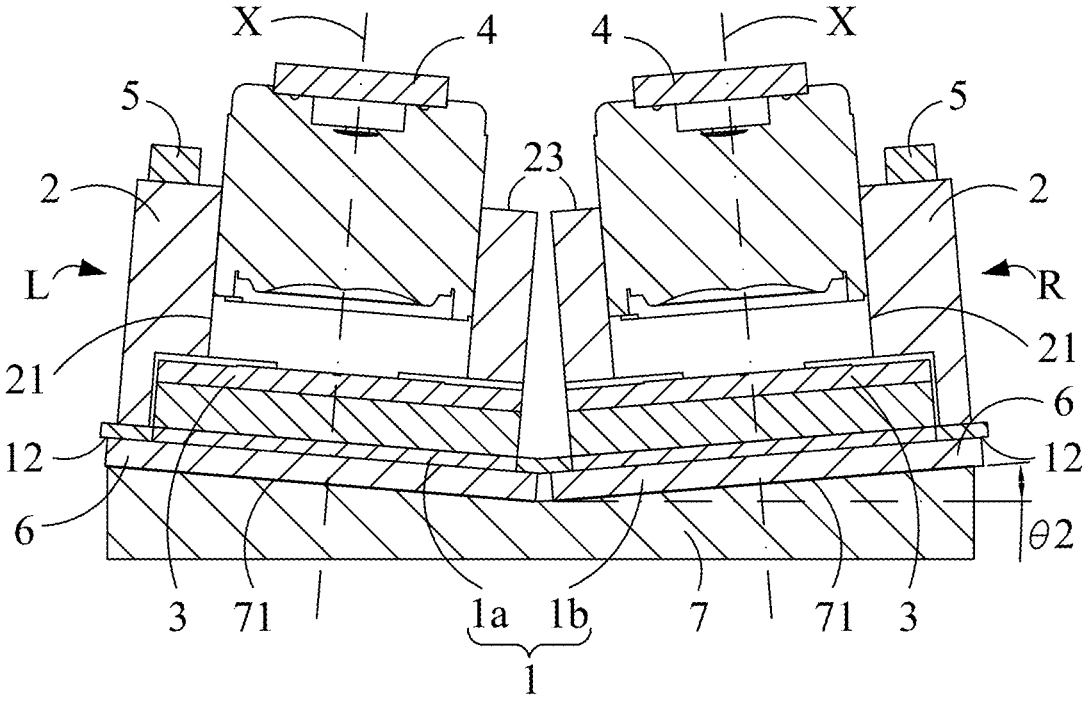
FIG. 3 is a cross-sectional view of the lens module taken along line A-A of FIG. 2.

Referring to FIG. 1 through FIG. 3, a lens module in an embodiment of the present disclosure comprises a substrate 1, two holders 2, two image sensors 3, and two lenses 4. The two holders 2 and the two image sensors 3 are disposed on the substrate 1. The two lenses 4 are disposed in the two holders 2 respectively.

The substrate 1 is at least one circuit board. The two holders 2 are disposed on the same circuit board or disposed respectively on two circuit boards electrically connected. In an embodiment, the substrate 1 is, for example, a flexible printed circuit (FPC), but the present disclosure is not limited thereto. The two holders 2 are, for example, fixed to the substrate 1 by UV curing.

The two image sensors 3 are disposed on the substrate 1 and disposed in the two holders 2 respectively, and thus the two image sensors 3 are enclosed by the two holders 2 respectively. For instance, with surface mount technology (SMT), the two image sensors 3 are positioned at solder paste printed on the substrate 1, and then the solder paste is melted by reflow soldering, allowing the two image sensors 3 to be electrically connected to the substrate 1. Thus, the substrate 1 enables the transmission of electrical signals of the two image sensors 3. For example, the substrate 1 provides MIPI, I2C, TTL, and DC voltage lead required for the two image sensors 3.

The lenses 4 each have an optical axis X. The optical axis X is an extension line that passes through the centers of the lenses 4. The two lenses 4 are disposed in the two holders 2 respectively. The optical axes X of the two lenses 4 pass through the two image sensors 3 respectively and meet in front of the substrate 1. Therefore, the two lenses 4 are not parallel to each other; instead, the two lenses 4 tilt toward each other. Each lens 4 comprises one or more optical lenses. The image sensors 3 are charge-coupled devices (CCD) or complementary metal-oxide semiconductors (CMOS), but the present disclosure is not limited thereto. The lenses 4 are fixed to the holders 2 respectively by, for example, UV curing, and located in front of the image sensors 3 respectively. Furthermore, the lenses 4 are firmly mounted on the holders 2 and separated from the image sensors 3 by a predetermined distance respectively, allowing focused images to be sharply formed on the image sensors 3.

In an embodiment of the present disclosure, the substrate 1 has a first region 1a and a second region 1b. The two image sensors 3 are disposed within the first region 1a and the second region 1b respectively. The substrate 1 has a partition line 11. The first region 1a and the second region 1b are separated by the partition line 11. The first region 1a and the second region 1b tilt such that the opposing edges of the first region 1a and the second region 1b are higher than the adjoining edges (at the partition line 11) of the first region 1a and the second region 1b. Preferably, the first region 1a and the second region 1b tilt symmetrically about the partition line 11, i.e., by the same tilt angle.

The lens module is divided into a left unit L and a right unit R whose positional relationship is indicated by the directions shown in FIG. 3. The left unit L comprises the first region 1a of the substrate 1 as well as the corresponding holder 2, image sensor 3 and lens 4 disposed within the first region 1a. The right unit R comprises the second region 1b of the substrate 1 as well as the corresponding holder 2, image sensor 3, and lens 4 disposed within the second region 1b. The two lenses 4 tilt toward each other such that the optical axes X meet in front of the substrate 1 to allow the left unit L and the right unit R to achieve binocular disparity, simulating human eyes seeing near objects.

Figure 4:
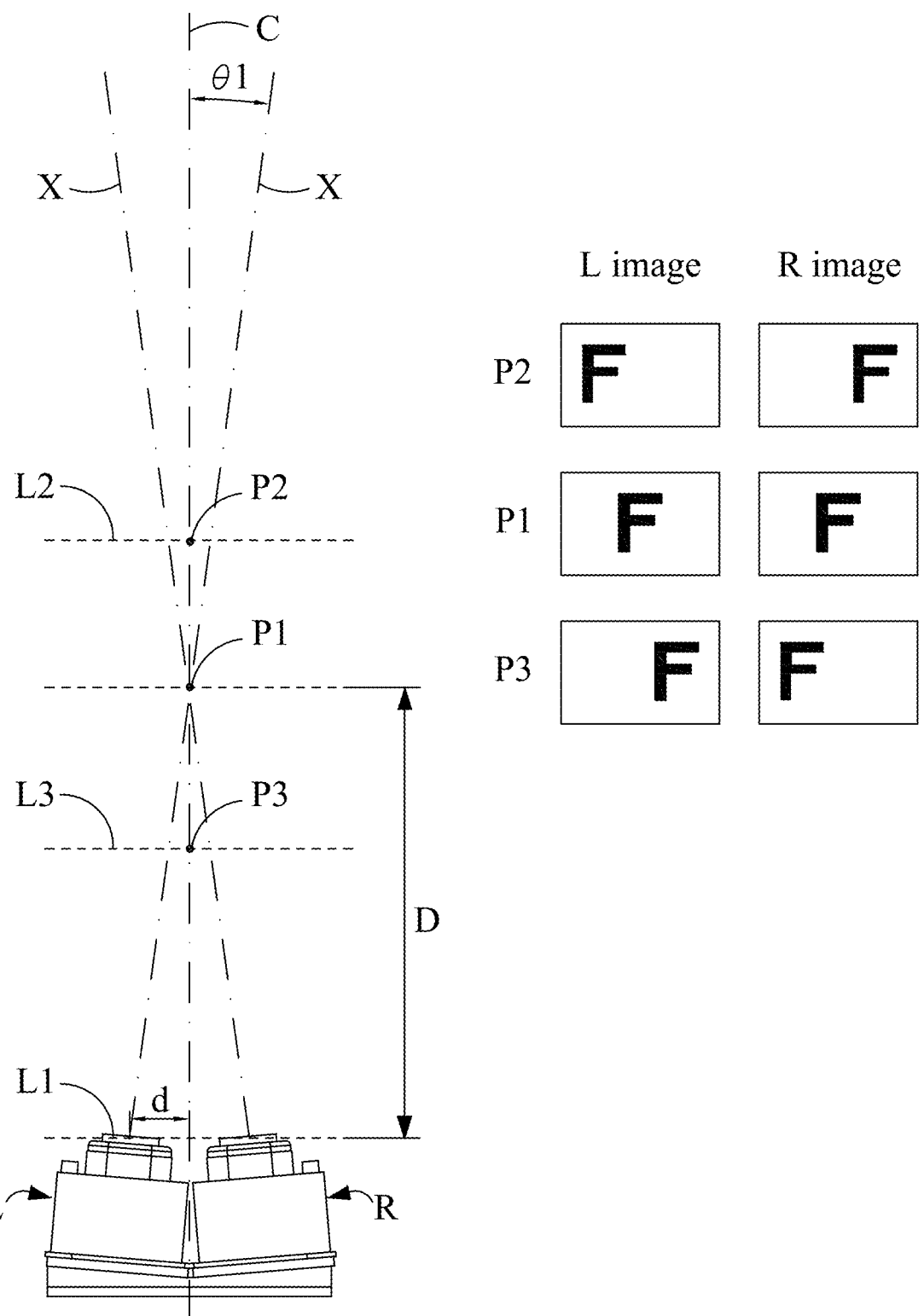
FIG. 4 shows on the left a schematic view of an optical structure of the lens module according to an embodiment of the present disclosure, and shows on the right pictures taken of three target objects F by a left unit and a right unit of the lens module.

Referring to the left diagram of FIG. 4, a reference line L1 in front of the two lenses 4 crosses the optical axis X of the left unit L and the optical axis X of the right unit R. A central axis C between the left unit L and the right unit R crosses the reference line L1 perpendicularly. The optical axis X of the left unit L and the optical axis X of the right unit R meet in front of the substrate 1, i.e., at a meeting point P1. The meeting point P1 lies on the central axis C and is separated from the reference line L1 by a distance D. The distance D is slightly less than the focal length of the two lenses 4. In an embodiment, a tilt angle θ1 is defined between the optical axis X and the central axis C. The tilt angle θ1 between the optical axis X of the left unit L and the central axis C is equal to the tilt angle θ1 between the optical axis X of the right unit R and the central axis C.

For example, three photographic target objects F are placed at three points, namely the meeting point P1, a first placing point P2, and a second placing point P3, on the central axis C respectively. The meeting point P1 lies between the first placing point P2 and the second placing point P3. The second placing point P3 is the nearest to the two lenses 4. Thus, the distance between the first placing point P2 and the reference line L1 is greater than the distance D, and the distance between the second placing point P3 and the reference line L1 is less than the distance D. A first auxiliary line L2 passes through the first placing point P2 and is parallel to the reference line L1. A second auxiliary line L3 passes through the second placing point P3 and is parallel to the reference line L1.

Referring to the right diagram of FIG. 4, the image captured of the photographic target object F at the meeting point P1 by the image sensor 3 of the left unit L is identical to the image captured of the photographic target object F at the meeting point P1 by the image sensor 3 of the right unit R, because both the two images are centrally located.

The image captured of the photographic target object F at the first placing point P2 by the image sensor 3 of the left unit L is located leftward, but the image captured of the photographic target object F at the first placing point P2 by the image sensor 3 of the right unit R is located rightward.

The image captured of the photographic target object F at the second placing point P3 by the image sensor 3 of the left unit L is located rightward, but the image captured of the photographic target object F at the second placing point P3 by the image sensor 3 of the right unit R is located leftward.

As described above, the images captured of the photographic target object F at the meeting point P1 by the left unit L and the right unit R are not deviated. The images captured of the photographic target object at a point farther than the meeting point P1, for example at the first placing point P2, by the left unit L and the right unit R being deviated outward. The images captured of the photographic target object at a point nearer than the meeting point P1, for example at the second placing point P3, by the left unit L and the right unit R being deviated inward. Therefore, owing to the binocular disparity achieved by the lens module, images captured by the left unit L and the right unit R have a three-dimensional sense when displayed on an appropriate display device, such as a 3D display screen or VR glasses.

Therefore, the lens module of the present disclosure is applied to endoscopes for capturing images such that the images thus captured have a stronger three-dimensional sense than images captured by conventional endoscopes, allowing the images thus captured to look real. The lens module of the present disclosure not only improves the approximation to reality in terms of human perception of the images thus captured but also enhances the precision of various operations and judgements. Thus, endoscopes equipped with the lens module of the present disclosure meet medical or industrial demand associated with strict operational precision requirements, for example, by being applied to minimally invasive brain surgery, for example, for use in brain thrombus removal, and enhancing surgery efficiency and success rate.

In an embodiment of the present disclosure, when the lens module is applied to endoscopes, with a distance d defined between the center of the front edge of each lens 4 and the central axis C, the relation between distance D and tilt angle $\theta 1$ is expressed as $d=D*\tan(\theta 1)$. For example, when distance D is around 15 mm, tilt angle $\theta 1$ is around 4.72°.

Referring to FIG. 1 through FIG. 3, in an embodiment of the present disclosure, the holders 2 are made of an opaque material and thus can enhance the light masking rate toward the image sensors 3, preventing other light beams from entering the holders 2 to the detriment of imaging quality.

In an embodiment of the present disclosure, the holders 2 each have a central hole 21 and a plurality of adhesive grooves 22. The central hole 21 penetrates an outer end surface 23 of the holder 2. The plurality of adhesive grooves 22 are disposed on the outer end surface 23 and are in communication with the central hole 21. A process of fixing the lenses 4 to the holders 2 respectively by UV curing entails allowing the lenses 4 to be penetratingly disposed at the central holes 21 respectively, allowing the plurality of adhesive grooves 22 to undergo UV curing accumulatively and fluidly, thereby allowing the lenses 4 to be firmly connected to the holders 2 respectively upon completion of the UV curing. Preferably, the plurality of adhesive grooves 22 are equiangularly arranged at the rim of each of the central holes 21 such that the lenses 4 are uniformly and firmly connected to the holders 2 respectively.

In an embodiment of the present disclosure, the lens module further comprises at least one light source 5 disposed on at least one of the two holders 2 to provide supplementary illumination to the front surroundings of the two holders 2. The light source 5 is, for example, a light-emitting diode (LED), an organic light-emitting diode (OLED), or any other appropriate and light-emitting electrically-controlled light-emitting component, but the present disclosure is not limited thereto. For instance, as shown in the diagram for an embodiment, a light source 5 is selectively mounted on each of the two holders 2. In an embodiment, one light source 5 is mounted at any position on one of the holders 2 to provide sufficient illumination to the two lenses 4. Thus, the lens module provides illumination spontaneously to enable images to be captured in dim or dark environment, enable the lens module to be applicable to endoscopes, and enable imaging to occur inside a human body or organ which lacks illumination. For example, in an embodiment, the light source 5 is selectively fixed to the holders 2 by UV curing, but the present disclosure is not limited thereto.

In an embodiment of the present disclosure, when the substrate 1 is a flexible printed circuit, the lens module further comprises two reinforcing plates 6. The two reinforcing plates 6 are connected to a rear surface 12 of the substrate 1 and correspond in position to the first region 1a and the second region 1b respectively. The reinforcing plates 6 are, for example, plate steel, but the present disclosure is not limited thereto. The reinforcing plates 6 are coupled to and fixed to the rear surface 12 of the substrate 1 by UV curing. The two reinforcing plates 6 augment the structural strength of the substrate 1 and thus are conducive to the stabilization of optical imaging.

In an embodiment of the present disclosure, the lens module further comprises an angle retaining seat 7. The angle retaining seat 7 has two adjoining surfaces 71. The two adjoining surfaces 71 tilt. The outward opposing edges of the two adjoining surfaces 71 are higher than the inward opposing edges of the two adjoining surfaces 71. The rear surface 12 of the substrate 1 is directly coupled to the two adjoining surfaces 71 of the angle retaining seat 7. Alternatively, the two reinforcing plates 6 are coupled to and fixed to the two adjoining surfaces 71 respectively (for example, by UV curing) such that the substrate 1 is indirectly connected to the angle retaining seat 7. Therefore, the left unit L and the right unit R tilt toward each other continuously because of the angle retaining seat 7.

In an embodiment of the present disclosure, the first region 1a and the second region 1b of the substrate 1 tilt symmetrically such that the same tilt angle $\theta 2$ is defined between a horizontal line and each of the two adjoining surfaces 71.

In an embodiment of the present disclosure, the angle retaining seat 7 has a direction mark 72 for recognizing the mounting direction of the angle retaining seat 7. Thus, the direction mark 72 assists with enhancing the ease of direction recognition in putting the substrate 1 and the angle retaining seat 7 together and assists with enhancing the ease of direction recognition in mounting the lens module on another object, such as an endoscope, so as to enhance assembly efficiency and precision. The direction mark 72 is, for example, a mark point, an arrow sign, a coarse surface, a dent point, or a chamfer (as shown in the diagram) on one of the end surfaces of the angle retaining seat 7, but the present disclosure is not limited thereto.

Figure 5:
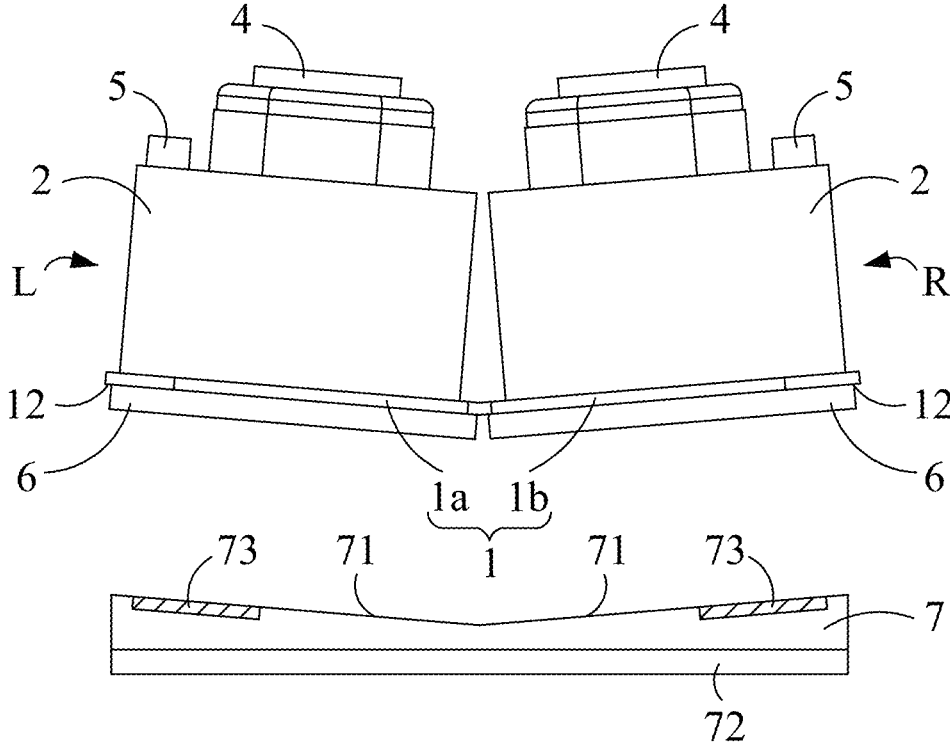
FIG. 5 is a lateral exploded view of the lens module according to an embodiment of the present disclosure.

Referring to FIG. 5, in an embodiment of the present disclosure, the angle retaining seat 7 has two piezoelectric layers 73. The two piezoelectric layers 73 are connected to the two adjoining surfaces 71 respectively. The piezoelectric layers 73 lie either above or below the adjoining surfaces 71. The two piezoelectric layers 73 correspond in position to the outward opposing edges of the two adjoining surfaces 71 respectively. Thus, the magnitude of a voltage applied to the two piezoelectric layers 73 is adjusted to control the extent of expansion of the two piezoelectric layers 73 and thereby alter the tilt of the first region 1*a* and the second region 1*b* of the substrate 1. Therefore, users may dynamically adjust the inward tilt of the left unit L and the right unit R relative to each other according to the positions of photographic target objects to instantly change and adjust the focal length of the lens module in the course of observation without replacing the lens module with another lens module of a different focal length to greatly enhance photographic quality and efficiency. For instance, referring to FIG. 4, in the absence of any voltage applied to the two piezoelectric layers 73, tilt angle θ1 is around 4.59°, and distance D is around 15 mm. Distance D can be adjusted to be around 20 mm by applying a voltage of around 100 V to the two piezoelectric layers 73 and changing the tilt angle θ1 to around 3.57°.

In an embodiment where the angle retaining seat 7 has two piezoelectric layers 73, the two adjoining surfaces 71 may not tilt, and the tilt of the first region 1*a* and the second region 1*b* of the substrate 1 can be controlled solely by the two piezoelectric layers 73. Alternatively, the two adjoining surfaces 71 tilt asymmetrically, and an input voltage applied to the two piezoelectric layers 73 is controlled to alter the tilt of the first region 1*a* and the second region 1*b* of the substrate 1.

The present disclosure is disclosed above by preferred embodiments. However, persons skilled in the art should understand that the embodiments are illustrative of the present disclosure only, but shall not be interpreted as restrictive of the scope of the present disclosure. Please note that all variations and replacements equivalent to the embodiments shall be deemed falling within the scope of the present disclosure. Therefore, the legal protection for the present disclosure shall be defined by the appended claims, and the scope of the appended claims must be given the broadest interpretation to encompass all amendments, similar arrangement, and process flow.

What is claimed is:

1. A lens module, comprising:
a substrate;
two holders disposed on the substrate;
two image sensors disposed on the substrate and disposed in the two holders respectively;
two lenses disposed in the two holders respectively, wherein optical axes of the two lenses pass through the two image sensors respectively and meet in front of the substrate; and
an angle retaining seat,
wherein the substrate has a first region and a second region, with the first and second regions separated by a partition line of the substrate, the two image sensors are disposed within the first region and the second region respectively, and the first region and the second region tilt such that outward opposing edges of the first region and the second region are higher than inward opposing edges of the first region and the second region, and
wherein the angle retaining seat has two adjoining surfaces, the two adjoining surfaces tilt such that outward opposing edges of the two adjoining surfaces are higher than inward opposing edges of the two adjoining surfaces, and a rear surface of the substrate is directly or indirectly coupled to the two adjoining surfaces.

2. The lens module of claim 1, further comprising two reinforcing plates connected to a rear surface of the substrate and corresponding in position to the first region and the second region of the substrate respectively.

3. The lens module of claim 1, wherein the angle retaining component seat has two piezoelectric layers connected to the two adjoining surfaces and corresponding in position to outward opposing edges thereof respectively.

4. The lens module of claim 1, wherein the angle retaining component seat has a direction mark for recognizing a mounting direction of the angle retaining component seat.

5. The lens module of claim 1, wherein the holders are made of an opaque material.

6. The lens module of claim 1, wherein the holders each have a central hole and a plurality of adhesive grooves, with the central hole penetrating an outer end surface of the holder, with the plurality of adhesive grooves being disposed on the outer end surface and being in communication with the central hole, allowing the lenses to be penetratingly disposed at the central holes respectively.

7. The lens module of claim 1, further comprising at least one light source disposed on at least one of the two holders.

* * * * *